(12) United States Patent
Kottenhahn et al.

(10) Patent No.: US 6,673,942 B1
(45) Date of Patent: Jan. 6, 2004

(54) RESOLUTION OF DL-RACEMIC MIXTURES

(75) Inventors: Matthias Kottenhahn, Freigericht (DE); Guenter Knaup, Bruchkoebel (DE); Karlheinz Drauz, Freigericht (DE); Meir Lahav, Rehovo (IL); David Zbaida, Givataim (IL)

(73) Assignees: Degussa AG, Duesseldorf (DE); Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 10/181,411

(22) PCT Filed: Feb. 11, 2000

(86) PCT No.: PCT/EP00/01112
§ 371 (c)(1),
(2), (4) Date: Jul. 23, 2002

(87) PCT Pub. No.: WO01/58835
PCT Pub. Date: Aug. 16, 2001

(51) Int. Cl.$^7$ .................. C07D 233/90; C07C 205/00; C07C 207/00; C07C 229/00; C07C 321/00
(52) U.S. Cl. ............... 548/339.1; 562/553; 562/559; 562/557; 562/561; 562/570; 562/573; 560/22
(58) Field of Search ............... 548/339.1; 562/553, 562/559, 557, 561, 570, 573

(56) References Cited

U.S. PATENT DOCUMENTS 4,864,031 A * 9/1989 Zbaida et al. ............... 548/344

FOREIGN PATENT DOCUMENTS

EP    0 225 503    6/1987

OTHER PUBLICATIONS

Harada, "The Optical Resolution of DL–Aspartic Acid, DL–Glutamic Acid, DL–Asparagine and DL–Gutamine by Preferential Crystallization" Bulletin of the Chemical Society of Japan, vol. 38(9), pp. 1552–1555 (Sep. 1965).*

Weissbuch et al, "Design of Polymeric Inhibitors for the Control of Crystal Polymorphism. Induced Enantiomeric Resolution of Racemic Histidine by Crystallization at 25C" J. Am. Chem. Soc., vol. 109, pp. 1869–1871 (1987).*

Shimon et al, "Design of Stereospecific Inhibitors for Crystal Dissolution" Molecular Crystals and Liquid Crystals, vol. 161, part pp. 199–219 (1988).*

Zbaida et al, "A Cyclic Continuous Process for Converting Conglomerates into Optically Pure Enantiomers by Crystallization an Dissolution with the assistance of 'Tailor–Made' Polymers" Tetrahedron, vol. 56, pp. 6645–6649 (Sep. 2000).*

* cited by examiner

*Primary Examiner*—Mukund J. Shah
*Assistant Examiner*—Zachary C. Tucker
(74) *Attorney, Agent, or Firm*—Oblon, Spivak, McClelland, Maier & Neustadt, P.C.

(57) ABSTRACT

The present invention relates to a process for the resolution of DL-racemic mixtures of compounds which crystalize in the form of a conglumerate. Both, the D and L-enantiomers are obtained according to the invention in a industrially feasable process by adding chiral enantioselective polymers to the supersaturated solution of the racemat to inhibit crystallization of one enantiomer. Next a DL-racemic mixture of said compound is suspended in about twice the amount of the crystallized enantiomer. Consequently, the opposite enantiomer could be recovered by said suspension by physical separation.

12 Claims, No Drawings

RESOLUTION OF DL-RACEMIC MIXTURES

This Application was filed under 35 U.S.C. 371, and is the U.S. national state PCT/EP00/01112, filed Feb. 11, 2000.

FIELD OF THE INVENTION

The present invention relates to a process for the resolution DL-racemic mixtures of chiral compounds which crystallize in the form of any conglomerate and some DL-racemic systems which exhibit various kinds of crystal twinning, such as microtwinning, lamellar macrotwinning as well as DL-racemic mixtures having different crystalline polymorphs, enabling the recovery of both the D and the L enantiomers. The invention farther provides an industrially feasible process for the optical resolution of such DL-racemates for continuously isolating both the D and L enantiomers.

BACKGROUND OF THE INVENTION

Among the large variety of existing methods for the resolution of enantiomers, only a few are suitable for a large scale industrial application. The classical method of spontaneous resolution, i.e. fractional crystallization of one enantiomer from a racemic supersaturated solution, usually by seeding the solution with seed crystals of the desired enantiomer, are still the most used, particularly for the resolution of DL-racemic mixtures which crystallize as conglomerates. These methods are, however, quite limited to systems which have no tendency for crystal twinning or in which there is a low barrier to spontaneous nucleation. In such cases the two enantiomers crystallize together spontaneously even in the presence of seeds of only one enantiomer. In accordance with many other known methods of resolution, a DL-racemic compound is reacted with an optically active reagent (resolving agent) to form a mixture of diastereoisomeric derivatives, e.g. by salt formation, which can be separated e.g. by fractional crystallization. Each of the thus isolated diastereoisomeric derivatives can then be decomposed to obtain the desired enantiomer of the initial DL-racemic compound. One of the drawbacks of these methods resides in the comparative large number of operational steps they involve.

The same applies to the traditional methods for resolving DL-racemates by selective enzymatic decomposition of a suitable derivative. For example the L-enantiomer of most of the amino acids can be isolated from their racemic N-acetyl-DL-ammo acid racemic mixtures by enantioselective hydrolysis of the N-acetyl-L-enantiomer using acylase I enzyme to afford the optically pure L-enantiomer.

Our U.S. Pat. No. 4,864,031 (the disclosure of which is incorporated herein by reference) describes a process for the kinetic resolution of DL-racemic mixtures crystallizing in the form of conglomerates from a supersaturated solution thereof by preferential crystallization in the presence of chiral crystal growth inhibitors that preclude or delay the nucleation of one enantiomorph, while leaving the opposite one unaffected, resulting in the preferential crystallization of the desired enantiomer. These chiral crystal growth inhibitors are carefully designed polymers consisting of a polymer backbone to which there is bound either the D or the L form of the compound to be resolved or of a modified derivative thereof. These polymeric inhibitors are effective in very small concentrations of up to about 3% by weight of the racemic mixture to be resolved.

Among the chiral polymeric crystal growth inhibitors disclosed in U.S. Pat. No. 4,864,031 and are also employed in the process according to the present invention are those listed below together with their abbreviations which would be used herein.

| | |
|---|---|
| L- or D- PAL | Poly-(N -acryloyl- L- or D-lysine) |
| L- or D- PMAL | Poly-(N -methacryloyl- L- or D-lysine) |
| L- or D- PGAH | Poly-[L- or D- -glutamyl (N-acryloyl hydrazide)] |
| L- or D- PA-Phe | Poly-(p-acrylamido L-or D-phenyl-alanine) |
| L- or D- PA-PAB-PHA | Poly-[N-acryloyl-(p-amiobenzoyl)-L- or D-sec-phenethylamide] |

The L- or D-enantiomer of the amino acid bound to the polymer will be chosen according to the L- or D-enantiomer, respectively, the crystallization of which is to be inhibited.

In the batchwise resolution, process according to the above-mentioned U.S. Pat. No. 4,864,031, by preferential crystallization of one enantiomer in the presence of an enantioselective polymer which inhibits the crystallization of the opposite enantiomer, there is left, after the separation of the crystallized enantiomer a mother liquor containing both the D and L enantiomers, the uncrystallized enantiomer being in excess, and the entire initial amount of the polymeric crystal growth inhibitor. In order to recover the opposite enantiomer which is present in the mother liquor in excess, the polymeric crystal growth inhibitor must be removed from the mother liquor. However, attempts to remove it by ultrafiltration were in most cases unsatisfactory for the following reasons: i) it is impossible to completely trap the polymer which owing to its random coil configuration penetrates through the ultrafiltration membrane under the pressure employed; ii) layers of the polymer accumulate on the surface of the ultrafiltration membrane, thereby decreasing its porosity and effectiveness; and iii) the ultrafiltration membrane is insufficiently stable during a prolonged filtration process, especially when the solution is highly acidic, such as an aqueous hydrochloric acid solution.

U.S. Pat. No. 4,864,031 also discloses a resolution method for the simultaneous recovery of both the D and L enantiomers where the DL-racemate is provided in two adjacent compartments of a resolution cell, separated by a suitable membrane which is permeable to the D- and L-enantiomers, but impermeable to the chiral polymeric inhibitor. To one compartment there is added an inhibitor of the D-enantiomer crystallization and to the other compartment—an inhibitor of the L-enantiomer crystallization. The result is that in the first compartment an essentially pure L-enantiomer is crystallized and in the other—an essentially pure D-enantiomer. This process was found to be too time consuming for industrial application, because of the low rates of passage of the solutions between the compartments, through the membrane due to the considerably small concentration differentials between the enantiomers in each compartment.

OBJECTS OF THE INVENTION

It is the object of the present invention to provide a process for the resolution of DL-racemic mixtures crystallizing as conglomerates, so as to recover each of the D and L-enantiomers in a substantially pure optical form, which process is adapted for large scale industrial application.

It is a further object of the invention to provide a process for the continuous resolution of DL-racemic mixtures crystallizing as conglomerates through repeated cycles of the above-mentioned resolution process by the addition of fresh amounts of the DL-racemic mixture in each cycle so as to recover increasing amounts of each of the D- and L-enantiomers.

SUMMARY OF THE INVENTION

The invention, in a first aspect thereof, provides a process for the resolution of a DL-racemic mixture of a compound crystallizing in the form of a conglomerate from a supersaturated solution thereof, to recover both the D and the L enantiomers, which process comprises the steps of:

a) effecting a preferential crystallization of one of said enantiomers from said supersaturated solution in the presence of an effective amount of a chiral enantioselective polymer which inhibits the crystallization of the opposite enantiomer;

b) physically separating the thus crystallized said one enantiomer to obtain a mother liquor comprising an excess of said opposite enantiomer;

c) adding to said mother liquor solid DL-racemic mixture of said compound in about twice the amount of said one enantiomer separated in step (b) and stirring the resulting suspension at a suitable temperature until substantially the entire suspended solid phase consists of said opposite enantiomer, and d) physically separating said solid opposite enantiomer, to obtain a solution having substantially the same composition as the initial solution used in step (a).

In a second aspect thereof the invention provides a continuous process for the resolution of DL-racemic mixture of a compound crystallizing in the form of a conglomerate from a supersaturated solution thereof, to recover both the D and the L enantiomers, the process comprising a plurality of cycles of steps a) to d) as described above wherein the supersaturated solution obtained in step d) of each cycle is submitted to the preferential crystallization in step a) of the next cycle and said cycle is repeated ad lib.

DETAILED DESCRIPTION OF THE INVENTION

The first step (a) of the resolution process of the invention is conducted in the same manner as described in U.S. Pat. No. 4,864,031, using the same chiral polymeric additives which enantioselectively inhibit the nucleation and growth of crystals of the enantiomer having the same chirality, without affecting the opposite enantiomer. The amounts of the chiral polymer that should be added in order to reach the desired result, range between about 1 to 3% by weight of the DL-racemic mixture in the solution. Separation of the precipitated enantiomer, e.g. by filtration, in step (b) affords this product at high chemical and optical yields. The use of seed crystals, of the enantiomer to be precipitated in this step is not required, but may, however, be desirable from the point of view of the rate of crystallization.

It has surprisingly been found, in accordance with the present invention that the opposite enantiomer can be successfully recovered in the above step c) in high chemical and optical yields, from the mother liquor obtained in step b) after separation of the crystallized first enantiomer, without the need to remove the polymeric crystal growth inhibitor (for the opposite enantiomer) which is present in this mother liquor in substantially its initial concentration, since the polymer is not occluded in the crystals of the first polymer precipitated in step a). In accordance with this finding of the invention, the opposite isomer is recovered in step c) by the addition to the mother liquor of solid DL-racemic mixture in about twice the amount of the first enantiomer isolated in step b) and stirring the resulting suspension at a suitable temperature, which is higher than the initial crystallization temperature in process a), until the suspension reaches an equilibrium at which point it was found that substantially the entire suspended solid phase consists of the opposite enantiomer of high optical purity. The crystallized opposite enantiomer is then separated by physical means, e.g. filtration.

Any attempt to dissolve the added solid DL-racemic mixture in step C) by heating the solution so as to form a clear solution rather than a suspension, would make it almost impossible to induce the crystallization of the opposite enantiomer, even though it is present in the solution in excess, owing to the presence in the solution of the enantioselective polymer which inhibits the nucleation and crystallization of this opposite enantiomer. In such a case, even seeding with seed crystals of the opposite enantiomer is of no avail and, if anything crystallizes at all, it will be most probably the other non-inhibited enantiomer.

It has been established that the suspension formed in step c) by the addition of the solid DL-racemic mixture to the mother liquor of step b), reaches an equilibrium after siring for about 7 to 19 hours at the optimal temperature. This optimal temperature is the one at which the amount of the opposite enantiomer which can be separated as a solid from the suspension after the prolonged sag is equal to the amount of the first enantiomer which crystallized in process step a). Separation of this solid opposite enantiomer leaves a solution having substantially the same composition as the original supersaturated solution of the DL-racemic mixture used in step a) and including substantially the initial amount of the polymeric crystal growth inhibitor which was present in the starting solution in step a). This resulting solution, can therefore, be subjected to a further cycle of process steps a) to d) so as to obtain additional amounts of pure D- and L-enantiomers. If process step c) is carried out at a lower temperature than the aforesaid optimal temperature, the amount of the added solid going into the solution will be reduced and consequently the amount of the solid obtained is higher and contains more of the DL-racemic mixture, i.e. the optical purity is lower. Conversely, if process step c) is conducted at a higher temperature than the optimal one, a larger amount of the added solid will dissolve in the solution, leading to a solution which contains in excess the opposite enantiomer of the one crystallized in step a).

It has also been found in accordance with the present invention that in cases where the process of the invention is to be applied to a DL-racemic mixture of a compound which is a hydrochloride salt and where aqueous hydrochloric acid is used as the solvent in process step a) in order to lower the solubility of the hydrochloric salt substrate, the optimal initial crystallization temperature is dependent on the concentration of this hydrochloric acid solution. The higher the concentration of the hydrochloric acid in the aqueous solution, the higher is the optimal temperature at which the crystallization of the desired enantiomer should be started and vice versa. This optimal temperature should thus be experimentally determined in each specific case where hydrochloric acid is used.

The process of the invention has been successfully applied to DL-racemic systems which exhibit various kinds of crystal twinning, such as microtwinning, lamellar macrotwinning as well as DL-racemic mixtures having different crystalline polymorphs and even where the thermodynamically most favorable polymorph is the crystalline racemate which precipitates regardless of the type of crystals used for seeding.

In accordance with a second aspect of the invention, the mother liquor obtained in process step d) which, as stated above, has substantially the same composition as the starting solution subjected to preferential crystallization in process step a), can be submitted to an additional cycle of process steps a) to d) which cycle can be repeated ad lib, thereby achieving continuous resolution of the DL-racemic mixture to recover the D- and the L-enantiomers at high chemical and optical yields. This continuous resolution process according to the invention has been achieved in a considerable number of various racemic mixtures which crystallize as conglomerates. As examples of such racemic mixtures, there can be mentioned DL-methionine hydrochloride (DL-Met.HCl), DL-glutamic acid hydrochloride (DL-Glu.HC-l), DL-histidine hydrochloride monohydrate (DL-His.HCl.H$_2$O), DL-asparagine monohydrate (DL-Asn.H$_2$O), DL-threonine (DL-Thr), DL-leucine hydrochloride (DL-Leu.HCl), DL-valine hydrochloride (DL-Val.HCl), DL-isoleucine hydrochloride (DL-Isoleu.HCL), DL-cysteine hydrochloride (DL-Cys.HCl) as well as DL-sec-phenethylalcohol-3,5-dinitrobenzoate.

The above procedure were performed with equal success with the DL-racemic mixtures of the corresponding hydrobromide salts to afford the enantiomeric hydrobromide salts.

The invention will be described in more detail in the following non-limiting examples.

EXAMPLE 1

Resolution of DL-methionine hydrochloride (DL-Met.HCl)

a) Crystallization of L-Met.HCl

DL-methionine (feed grade) (45 g, equivalent to 55.87 g of DL-Met.HCl) was dissolved by heating and stirring in 105 ml of aqueous concentrated (32%) hydrochloric acid and the solution was cooled to room temperature. 0.9 g of poly-(N methacryloyl-D-lysine) (D-PMAL) was dissolved in 7.5 ml of water at room temperature and the resulting solution was added to the methionine hydrochloride solution. The HCl concentration in the resulting solution was about 22%. The combined clear solution was seeded with L-methionine hydrochloride seed crystals (3 mg) and placed in a thermostated cooling bath. The starting temperature of crystallization was 13° C. which was decreased to 6° C. at a rate of 0.5° C. per hour for the first 2 hrs, and 1° C. every further hour, down to 6° C. The solution was then left at 6° C. for one hour. Mechanical stirring was started after 3–4 hrs from the start of the crystallization and continued regularly till the end of the crystallization process. (Alternatively, the stirring can start at the beginning of the crystallization without affecting the end result). The precipitated small needle-like crystals were filtered through a sintered glass filter (No. 1) and dried. 6.69 g (23.9%) of L-Met.HCl were obtained consisting of 97% L and 3% D (by chiral G.C. and H.P.L.C. analysis). A sample of the product was washed with 37% hydrochloric acid to obtain crystals consisting of 98.74% L- and 1.26% D-Met.HCl.

b) Recovery of the D-Met.HCl 13.4 g of solid powdered DL-Met.HCl were added to the mother liquor obtained in step (a) above, and the resulting slurry was stirred at 19.2° C. for 7–17 hrs. The precipitate was then filtered off to obtain 7.13 g of a mixture composed of 1.72 g of DL-Met.HCl and 5.41 g of D-Met.HCl. It follows that 11.68 g of DL-Met.HCl were introduced into the mother liquor, resulting in a new solution comprising 27.28 g of L-Met.HCl and 28.16 g of D-Met.HCl and having an L/D ratio of 49.2/50.8% which can be subjected to a repeated crystallization of the L-Met.HCl as in step (a) above.

Correlation between the optimal initial crystallization temperature (the temperature at which the crystallization starts) at various hydrochloric acid concentrations and the optimal temperature for step (b) is illustrated in the following Table I.

TABLE 1

Correlation between the initial crystallization temperature of L-Met.HCl and the temperature of recovery of D-Met.HCl.

| Initial L-Met.HCl crystallization temperature (° C.) | D-Met.HCl recovery temperature (° C.) |
| --- | --- |
| 9.8–9.9 | 17.4 |
| 10.2 | 17.9–18 |
| 11.8–11.9 | 18.9–19 |
| 13.3–13.5 | 19.2 |
| 13.9 | 19.5 |
| 15.8 | 23.8 |

EXAMPLE 2

Continuous Isolation of L-Met.HCl and D-Met.HCl

The mother liquor obtained in Example 1(a) above was recrystallized as described in that Example to afford 5.5 g of L-Met.HCl composed of 96% L and 4% D (by chiral G.C. and H.P.L.C. analysis).

To the mother liquor obtained above there were added 12.5 g of solid powdered DL-Met.HCl and the resulting suspension was stirred for 8 hrs at 19.2° C. and then filtered to obtain 5.5 g of a solid mixture composed of 0.5 g of DL-Met.HCl and 5 g of D-Met.HCl. Therefore, 12 g of DL-Met.HCl were introduced into the solution.

The above procedure was repeated for 18 more cycles and the L-Met.HCl and D-Met.HCl were collected separately. In general, the amounts of solid powdered DL-Met.HCl added in each cycle to the mother liquor obtained after the filtration of the crystallized L-Met.HCl, ranged between 2 to 2.7 times the amount of the L-Met.HCl recovered in the preceding step.

Some losses of the viscous DL-Met.HCl containing solution have been observed in each cycle, which explains the gradually decreasing amount of L an D-Met.HCl collected. The results of the first 20 cycles (including examples 1 and 2) are summarized in the following Table II.

TABLE 11

Continuous separation of L and D-Met.HCl over the first 20 cycles

| Cycle No. | Amount of L-Met.HCl recovered (g) | Amount of D-Met.HCl recovered (g) |
| --- | --- | --- |
| 1 (Example 1) | 6.69 | 5.41 |
| 2 (Example 2) | 5.50 | 5 |
| 3 | 5.76 | 4.91 |
| 4 | 5.31 | 4.30 |
| 5 | 5.19 | 4.40 |
| 6 | 4.80 | 4.18 |
| 7 | 4.57 | 4.18 |
| 8 | 3.61 | 3.58 |
| 9 | 4.35 | 3.63 |
| 10 | 3.72 | 3.29 |
| 11 | 3.55 | 3.32 |
| 12 | 3.43 | 3.2 |
| 13 | 2.99 | 2.7 |
| 14 | 2.96 | 2.68 |
| 15 | 2.66 | 2.55 |
| 16 | 2.18 | 2.26 |

TABLE 11-continued

Continuous separation of L and D-Met.HCl over the first 20 cycles

| Cycle No. | Amount of L-Met.HCl recovered (g) | Amount of D-Met.HCl recovered (g) |
|---|---|---|
| 17 | 2.04 | 1.9 |
| 18 | 2.3 | 2.1 |
| 19 | 2.02 | 1.8 |
| 20 | 1.8 | 1.6 |

EXAMPLE 3

The procedure of Examples 1 and 2 was repeated except that the initial supersaturated solution included L-PMAL instead of D-PMAL. Therefore, D-Met.HCl crystallized in the first step (a) and the mother liquor obtained after the filtration of this product included an excess of L-Met.HCl, which could be recovered therefrom by the procedure of Example 1(b) above. Repeated cycles of these operations afforded the D- and L-Met.HCl in substantially the same amounts as given in Table II above.

EXAMPLES 4 to 21

The L and D enantiomers were separated by the procedure of Example 1 in the following systems: Glu.HCl, His.HCl.H$_2$O, Asn.H$_2$O, Thr, Leu.HCl, Val.HCl, Isoleu.HCl, Cys.HCl and sec-phenethyl 3,5-dinitrobenzoate.

In all the above separations the DL-racemic mixtures and the chiral polymeric crystal growth inhibitor were dissolved by heating in the reaction solvents and the clear solutions were left at about 22° C. for 9 hrs with or without continuous stirring. The precipitated crystals collected by filtration possessed an enantiomeric excess* in the range of 94–98%. Solid powdered DL-racemic mixtures were added to the mother liquors and the resulting slurries were stirred at about 26° C. for 8–17 hrs. The suspended solids were filtered off and in some cases were recrystallized to reach an enantiomeric excess in the range of 85–90%. The conditions and results are summarized in the following Table III.

* Enantiomeric excess %=(%L-%D)/(%LD) or vice versa.

TABLE III

Separation of D and L enantiomers in different systems

| | | Step (a) | | | Step (b) | | | |
|---|---|---|---|---|---|---|---|---|
| Example No. | DL-racemic mixture of | concentration and solvent | Polymeric inhibitor (% by wt. of racemic mixture) | Precipitated Enantiomer | amount obtained (g) | amount of DL-mixture added (g) | precipitated enantiomer | amount obtained (g) |
| 4 | Glu.HCl | 5 g/20 ml aq. HCl 5N | L-PAL or L-PMAL or L-PGAH (2%) | D-Glu.HCl | 1.1 | 2.3 | L-Glu.HCl | 1 |
| 5 | Glu.HCl | 5 g/20 ml aq. HCl 5N | D-PAL or D-PMAL or D-PGAH (2%) | L-Glu.HCl | 1.1 | 2.3 | D-Glu.HCl | 1 |
| 6 | His.HCl.H$_2$O | 4 g/10 ml H$_2$O | L-PA-Phe (3%) | D-His.HCl.H$_2$O | 0.5 | 1.05 | L-His.HCl.H$_2$O | 0.44 |
| 7 | His.HCl.H$_2$O | 4 g/10 ml H$_2$O | D-PA-Phe (3%) | L-His.HCl.H$_2$O | 0.5 | 1.05 | D-His.HCl.H$_2$O | 0.45 |
| 8 | Asn.H$_2$O | 2 g/20 ml H$_2$O | L-PAL or L-PMAL (2%) | D-Asn.H$_2$O | 0.4 | 0.83 | L-Asn.H$_2$O | 0.34 |
| 9 | Asn.H$_2$O | 2 g/20 ml H$_2$O | D-PAL or D-PMAL (2%) | L-Asn.H$_2$O | 0.4 | 0.83 | D-Asn.H$_2$O | 0.33 |
| 10 | Thr | 7.5 g/25 ml H$_2$O | L-PAL or L-PMAL (1.8%) | D-Thr | 1.8 | 3.7 | L-Thr | 1.53 |
| 11 | Thr | 7.5 g/25 ml H$_2$O | D-PAL or D-PMAL (1.8%) | L-Thr | 1.8 | 3.7 | D-Thr | 1.55 |
| 12 | Leu.HCl | 4 g/32 ml aq. HCl 32% (11N) | L-PAL or L-PMAL (1.8%) | D-Leu.HCl | 0.4 | 0.84 | D-Leu.HCl | 0.35 |
| 13 | Leu.HCl | 4 g/32 ml aq. HCl 32% (11N) | L-PAL or L-PMAL (1.8%) | L-Leu.HCl | 0.41 | 0.85 | D-Leu.HCl | 0.36 |
| 14 | Val.HCl | 4 g/15 ml aq. HCl 32% (11N) | L-PAL or L-PMAL (2%) | D-Val.HCl | 0.2 | 0.42 | L-Val.HCl | 0.17 |
| 15 | Val.HCl | 4 g/15 ml aq. HCl 32% (11N) | D-PAL or D-PMAL (2%) | L-Val.HCl | 0.2 | 0.42 | D-Val.HCl | 0.18 |
| 16 | Isoleu.HCl | 7 g/15 ml aq. HCl 32% (11N) | L-PAL or L-PMAL (1%) | D-Isoleu.HCl | 1.01 | 2.2 | L-Isoleu.HCl | 0.9 |

TABLE III-continued

Separation of D and L enantiomers in different systems

| | | Step (a) | | | Step (b) | | | |
|---|---|---|---|---|---|---|---|---|
| Example No. | DL-racemic mixture of | concentration and solvent | Polymeric inhibitor (% by wt. of racemic mixture) | Precipitated Enantiomer | amount obtained (g) | amount of DL-mixture added (g) | precipitated enantiomer | amount obtained (g) |
| 17 | Isoleu.HCl | 7 g/15 ml aq. HCl 32% (11N) | D-PAL or D-PMAL (1%) | D-Isoleu.HCl | 1 | 2.1 | D-Isoleu.HCl | 0.9 |
| 18 | Cys.HCl | 6.8 g/4 ml aq. HCl 32% (11N) | L-PAL or L-PMAL (2%) | D-Cys.HCl | 0.65 | 1.37 | L-Cys.HCl | 0.59 |
| 19 | Cys.HCl | 6.8 g/4 ml aq. HCl 32% (11N) | D-PAL or D-PMAL (2%) | L-Cys.HCl | 0.7 | 1.11 | D-Cys.HCl | 0.6 |
| 20 | sec-phenethyl 3,5-dinitro-benzoate | 4.5 g/1.5 ml toluene/4.5 ml DMF | L-PA-PAB-PHA (1%) | D-sec-phenethyl 3,5-dinitrobenzoate | 0.66 | 1.33 | L-sec-phenethyl 3,5-dinitrobenzoate | 0.59 |
| 21 | sec-phenethyl 3,5-dinitro-benzoate | 4.5 g/1.5 ml toluene/4.5 ml DMF | D-PA-PAB-PHA (1%) | L-sec-phenethyl 3,5-dinitrobenzoate | 0.67 | 1.34 | D-sec-phenethyl 3,5-dinitrobenzoate | 0.58 |

What is claimed is:

1. A process for the resolution of a DL-racemic mixture of a compound crystallizing in the form of a conglomerate from a supersaturated solution thereof, to recover both the D and the L enantiomers, which process comprises the steps of:
   a) effecting a preferential crystallization of one of said enantiomers from said supersaturated solution in the presence of an effective amount of a chiral enantioselective polymer which inhibits the crystallization of the opposite enantiomer;
   b) physically separating the thus crystallized said one enantiomer to obtain a mother liquor comprising an excess of said opposite enantiomer;
   c) adding to said mother liquor solid DL-racemic mixture of said compound in about twice the amount of said one enantiomer separated in step (b) and stirring the resulting suspension at a suitable temperature until substantially the entire suspended solid phase consists of said opposite enantiomer; and
   d) physically separating said solid opposite enantiomer, to obtain a solution having substantially the same composition as the initial solution used in step (a).

2. A process according to claim 1 wherein the crystallized said one enantiomer is separated in step (b) by filtration.

3. A process according to claim 2 wherein said solid opposite enantiomer is separated in step (d) by filtration.

4. A process according to claim 1, wherein step (a) is carried out in aqueous solvent.

5. A process according to claim 4 wherein said compound is a hydrochloride salt and step (a) is carried out in aqueous hydrochloric acid.

6. A process according to claim 1, wherein said compound to be resolved is a DL-amino acid.

7. A process according to claim 6, wherein said DL-amino acid is selected from DL-glutamic acid hydrochloride, DL-histidine monohydrochloride monohydrate, DL-asparagine monohydrate, DL-threonine, DL-leucine hydrochloride, DL-valine hydrochloride, DL-isoleucine hydrochloride and DL-cysteine hydrochloride.

8. A process according to claim 6, wherein said DL-amino acid is DL-methionine hydrochloride.

9. A process according to claim 1, wherein said compound to be resolved is DL-sec-phenethyl-3,5-dinitrobenzoate.

10. A process according to claim 1, wherein the enantioselective polymer used in step (a) has an L-chirality and inhibits the crystallization of the L-enantiomer of said compound so that said one enantiomer crystallizing in step (a) is the D-enantiomer and said opposite enantiomer separated in step (d) is the L-enantiomer.

11. A process according to claim 1, wherein the enantioselective polymer used in step (a) has a D-chirality and inhibits the crystallization of the D-enantiomer of said compound so that said one enantiomer crystallizing in step (a) is the L-enantiomer and said opposite enantiomer separated in step (d) is the D-enantiomer.

12. A continuous process according to claim 1, which comprises a plurality of cycles of operational steps (a) to (d) wherein said supersaturated solution obtained in step (d) of each cycle is submitted to the preferential crystallization in step (a) of the next cycle.

* * * * *